United States Patent [19]

Bazan et al.

[11] Patent Number: 5,621,110
[45] Date of Patent: Apr. 15, 1997

[54] PROCESS FOR PREPARING N-ACYLATED 4-HYDROXYPENYLAMINE DERIVATIVES WITH ANALGESIC PROPERTIES

[75] Inventors: Nicolas G. Bazan, New Orleans, La.; Julio Alvarez-Builla Gomez, Alcala De Henares, Spain

[73] Assignee: LSU Medical Center Foundation, New Orleans, La.

[21] Appl. No.: 529,549

[22] Filed: Sep. 18, 1995

Related U.S. Application Data

[62] Division of Ser. No. 426,234, Apr. 21, 1995, Pat. No. 5,554,636.
[51] Int. Cl.$^6$ ............................................. C07D 275/06
[52] U.S. Cl. ............................................................. 548/210
[58] Field of Search ............................................. 548/210

[56] References Cited

U.S. PATENT DOCUMENTS 4,116,964  9/1978  Zinnes et al. .......................... 260/294.8

OTHER PUBLICATIONS

Hsi et al., J. Labelled Compd. Radiopharm. (1989), 27(3), 287–95.
Easton et al., J. Chem. Soc., Perkin Trans. 1(1990), (2), 277–82.
D'Amico et al., J. Heterocycl. Chem. (1988), 25(4), 1183–90.

*Primary Examiner*—Joseph McKane
*Assistant Examiner*—Laura Cross
*Attorney, Agent, or Firm*—Finnegan, Henderson, Farabow, Garrett and Dunner

[57] ABSTRACT

The present invention relates to a series of new N-acylated 4-hydroxyphenylamine derivatives, linked via an alkylene bridge to the nitrogen atom of a 1,2-benzisothiazol-3(2H)-one 1,1-dioxide group of formula I:

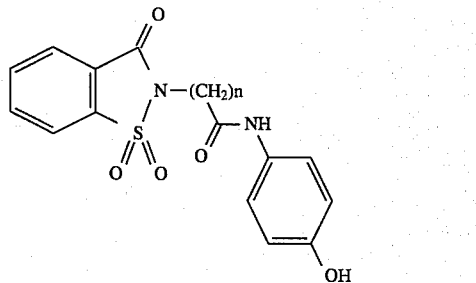

in which n is a number from 1 to 5, and to processes for preparing these derivatives and to pharmaceutical compositions containing said derivatives; these compounds possess high analgesic activity free from antipyretic activity, and they display little hepatotoxic effect.

1 Claim, 5 Drawing Sheets

PROCESS FOR PREPARING N-ACYLATED 4-HYDROXYPENYLAMINE DERIVATIVES WITH ANALGESIC PROPERTIES

This is a division of application Ser. No. 08/426,234 filed Apr. 21, 1995 now U.S. Pat. No. 5,554,636.

FIELD OF THE INVENTION

The present invention relates to a series of new N-acylated 4-hydroxyphenylamine derivatives, to processes for preparing them and to pharmaceutical compositions containing said derivatives.

These compounds possess analgesic activity free from antipyretic activity and with little hepatotoxic effect, as a result of which they may be much more useful than paracetamol and other nonsteroidal analgesics (NSAIA) in the treatment of chronic pain and in situations in which a decrease in body temperature is not indicated. For example, these compounds could be used in patients in whom analgesia is indicated but in whom it is also desired to maintain the body temperature modulating mechanisms in order to protect the body against infection, as occurs in postoperative processes.

BACKGROUND OF THE INVENTION

Analgesics such as paracetamol and other NSAIA type drugs have been used for some time for the treatment of pain and/or as antipyretics, this dual action sometimes being contraindicated. Moreover, the high death rate associated with their hepatotoxic activity means that due care must be exercised when administering these drugs.

For this reason, the need remains in this field to search for new, more selective molecules with greater pharmacological potency and little hepatotoxic effect, and which do not, if possible, possess the antipyretic effect generally associated with the already known types of drug.

The present invention includes a series of new N-acylated 4-hydroxyphenylamine derivatives, linked via an alkylene bridge to the nitrogen atom of a 1,2-benzisothiazol-3(2H)-one 1,1-dioxide group.

It has been ascertained that, surprisingly, these compounds possess high analgesic activity free from antipyretic activity, and that they display, in addition, little hepatotoxic effect. Moreover, they are available on an industrial scale, so that they prove satisfactory from the standpoint of their possible therapeutic application in the clinical situation, and thus from the standpoint of their practical application.

SUMMARY OF THE INVENTION

The present invention relates to a series of new N-acylated 4-hydroxyphenylamine derivatives, linked via an alkylene bridge to the nitrogen atom of a 1,2-benzisothiazol-3(2H)-one 1,1-dioxide group, of general formula I:

in which n is a number from 1 to 5.

Some specific examples of the present invention, without, however, limiting it, are the following:

2-[2,3-dihydro-3-oxo-1,2-benzisothiazol-2-yl 1,1-dioxide]-N-(4-hydroxyphenyl) acetamide.
3-[2,3-dihydro-3-oxo-1,2-benzisothiazol-2-yl 1,1-dioxide]-N-(4-hydroxyphenyl) propionamide.
4-[2,3-dihydro-3-oxo-1,2-benzisothiazol-2-yl 1,1-dioxide]-N-(4-hydroxyphenyl) butanamide.
5-[2,3-dihydro-3-oxo-1,2-benzisothiazol-2-yl 1,1-dioxide]-N-(4-hydroxyphenyl) pentanamide.
6-[2,3-dihydro-3-oxo-1,2-benzisothiazol-2-yl 1,1-dioxide]-N-(4-hydroxyphenyl) hexanamide.

The compounds of general formula I may be prepared by means of standard, already known processes described in the literature, and which are indicated below.

Thus,

A) a compound of formula II, in which "n" has already been defined above, is reacted with a compound of formula III where Me is an alkali metal such as sodium or potassium, to give rise to a compound of formula I already defined above.

Or alternatively,

B) a compound of formula IV, in which "n" has already been defined above, is reacted with 4-aminophenol to give a compound of formula I.

For example, the alkylation indicated in A) may be performed in a manner similar to the process described by H. L. Rice and G. R. Pettit in J. Am. Soc. 76, 302 (1954).

The amidation indicated in B) may be carried out by means of any of the numerous methods described in the literature, either by means of reaction between the corresponding acid chloride of the compound of general formula IV, obtained previously, and 4-aminophenol, or alternatively by means of direct reaction between the acid of general formula IV and 4-aminophenol, employing a dehydrating agent such as dicyclohexylcarbodiimide, in a manner similar to the one described by G. Fölsch in Chem. Scand., 13, 1407 (1959).

The starting materials of general formulae II, III and IV are known or may be prepared by means of standard processes from commercial reactants.

The present invention also includes the formation of pharmaceutically acceptable, stable salts of the compounds of formula I, with metals or amines. Examples of metals used as cations are alkali metals such as Na or K and alkaline-earth metals such as Mg and Ca. Examples of amines include N,N-dibenzylethylenediamine, chloroprocaine, choline, diethanolamine, ethylenediamine, N-methylglucamine and procaine.

The compounds of the present invention may be administered alone, but they will generally be administered mixed with a pharmaceutical vehicle selected in accordance with the administration route and standard pharmaceutical practice. For example, they may be administered orally, either in the form of tablets containing excipients such as starch or lactose, or in capsules, either alone or mixed with excipients, or in the form of syrups or suspensions containing coloring or flavoring agents. They may also be injected parenterally, for example intramuscularly, intravenously or subcutaneously. In parenteral administration, they can preferably be used in the form of a sterile aqueous solution which can contain other solutes, such as, for example, any salt or glucose in order to make the solution isotonic.

The compounds of the present invention may be administered to man for the treatment of pain, for example orally, either covered in gelatin capsules or compressed in lozenges. For oral therapeutic administration, said compounds may be mixed with excipients and used in the form of lozenges, tablets, capsules, elixirs, suspensions, syrups, wafers, chewing gum, and the like. These preparations could contain at least 0.5% of active compound, but can vary depending on each form, in particular between 4% and 75% approximately of the weight of each unit. The amount of active compound in such compositions should be that which is necessary for obtaining the corresponding dosage. The compositions and preparations obtained according to the present invention are prepared in such a way that each oral dosage unit can contain between 0.1 and 300 mg of the active compound.

In parenteral therapeutic administration, the active compounds of this invention should be incorporated in a solution or suspension. These preparations could contain at least 0.1% of the active compound, but can vary between 0.5% and 50% approximately of the weight of the preparation. The amount of active compound in such compositions should be that which is necessary for obtaining the corresponding dosage. The compositions and preparations obtained according to the present invention are prepared in such a way that each parenteral dosage unit can contain between 0.5 and 100 mg of the active compound. While intramuscular administration may be given in a single dose or divided into up to three doses, intravenous administration can include a drip device for giving the dose by venoclysis. Parenteral administration of the preparation may be performed by means of ampoules, disposable syringes or multiple-dose vials made of glass or plastic.

Of necessity, there will be variations which will depend on the weight and conditions of the subject to be treated and on the particular administration route selected.

The reaction conditions employed in the variants A) and B) are as follows:

The solvents which are envisaged are water and all inert organic solvents such as alcohols, for example methanol, ethanol, isopropanoland n-butanol; ethers, for example lower dialkyl ethers such as diethyl ether, tertbutyl methyl ether, diisopropyl ether or cyclic ethers such as tetrahydrofuran and dioxane; lower aliphatic carboxylic acids such as acetic and propionic acids, lower dialkylformamides such as dimethylformamide; lower alkyl nitriles such as acetonitrile; dimethyl sulfoxide; and liquid heteroaromatic bases such as pyridine. Mixtures of solvents, including water, may also be employed. If necessary, the reactants may be reacted without solvents.

The reaction temperature can vary between $-10°$ and $160°$ C., and preferably between $0°$ and $150°$ C. The reaction is normally carried out at the boiling point of the solvent used.

The reaction may be performed at normal pressure, but also under high pressure. It is generally performed at normal pressure.

The reaction time varies between 2 and 3 hours.

According to the invention, the separation and isolation of the product formed in the course of the reaction are carried out by means of technigues commonly used for this purpose, it being possible to subject the product to a traditional purification such as recrystallization, distillation or chromatography.

Analgesic activity was measured in CD-1 mice (Charles-River) on the basis of the following three methods:

In the tail flick method (D'Amour, F. E., Smith, D. L., J. Pharmacol. Exp. Ther. 72, 74, 1941), the tail of each mouse is exposed to a concentrated light beams when the animal feels pain, it removes its tail abruptly from said beam, and the latency time of this flick response is measured. The compound indicated by each symbol was administered orally to groups of 10 mice at the doses indicated as abscissae. The analgesia was quantified before and 15, 30, 60 and 120 minutes after the administration of each compound. The peak activity (30 minutes) was plotted as the percentage of mice in which the latency time for flicking the tail was at least doubled.

The second method employed is the hotplate method (Wolfe, G. and MacDonald, A. D., J. Pharmacol. Exp. Ther. 80, 300, 1944). The mouse is placed on a plate at $54°$ C., and the latency time of withdrawal of a hind foot or a jump is measured. Groups of 10 mice, to which the compounds were administered orally at the doses indicated as abscissae, were subjected to the hotplate test before and at the end of 30 and 60 minutes following administration of the compounds. The mean latency at 30 and 60 minutes minus the baseline latency is plotted as ordinates.

The third method consists in measuring the number of writhes performed by a mouse as a manifestation of the pain produced by an intraperitoneal injection of 10 mL/kg of 0.4% acetic acid solution. The measurements were carried out in parallel fashion in animals which were injected with the vehicle (Suspension K, Bioserve, Frenchtown, New Jersey, USA), the standard drugs (paracetamol, morphine) or the test compound. Following oral administration of each compound, the mice (groups of 8 or more) received, 25 minutes later, an intraperitoneal injection of 10 mL/kg of 0.4% acetic acid. The number of writhes was counted 5–15 minutes after the injection of acetic acid. The percentage of the number of writhes obtained in control mice (31±2.3) is plotted as ordinates.

Figure 1:
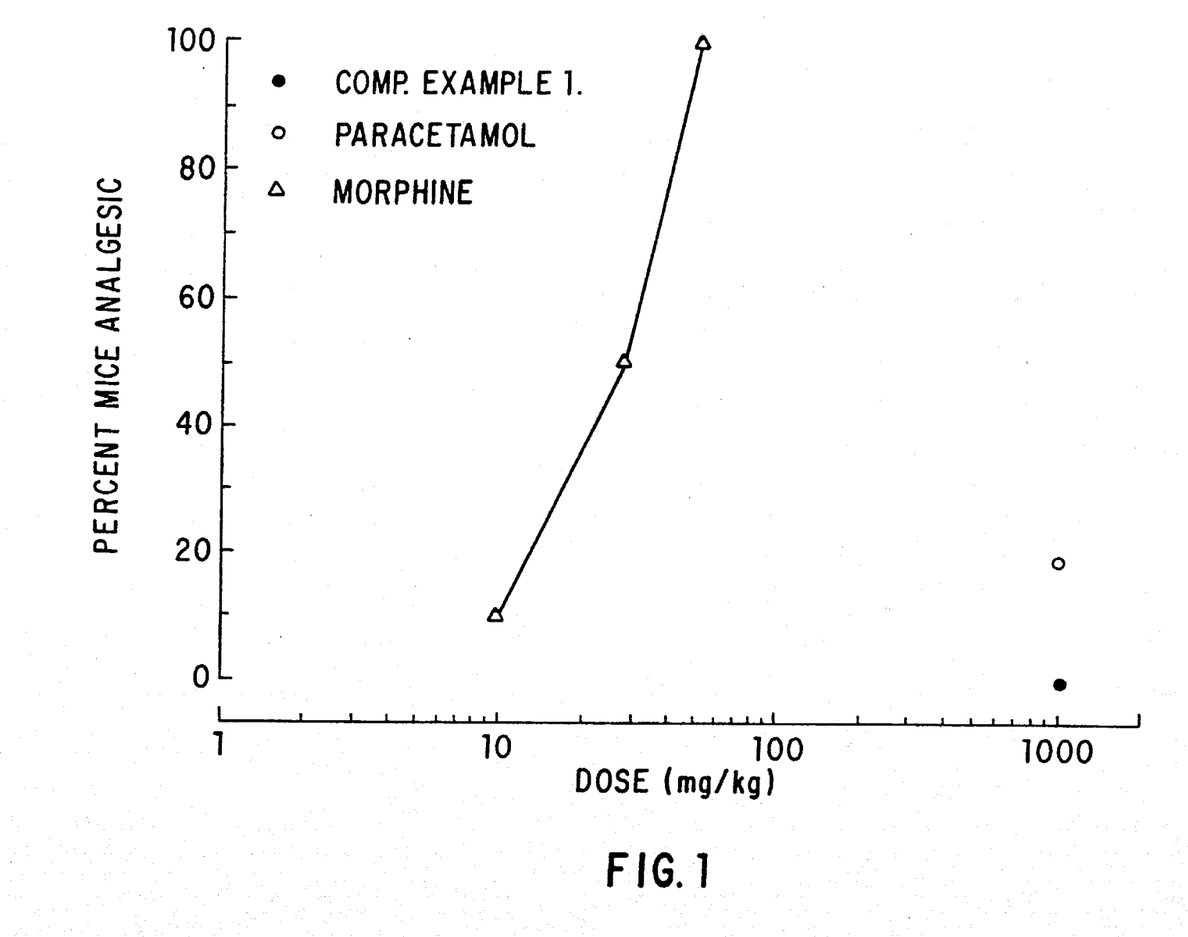
FIG. 1 is the analgesic effect of the tail flick test.
Figure 2:
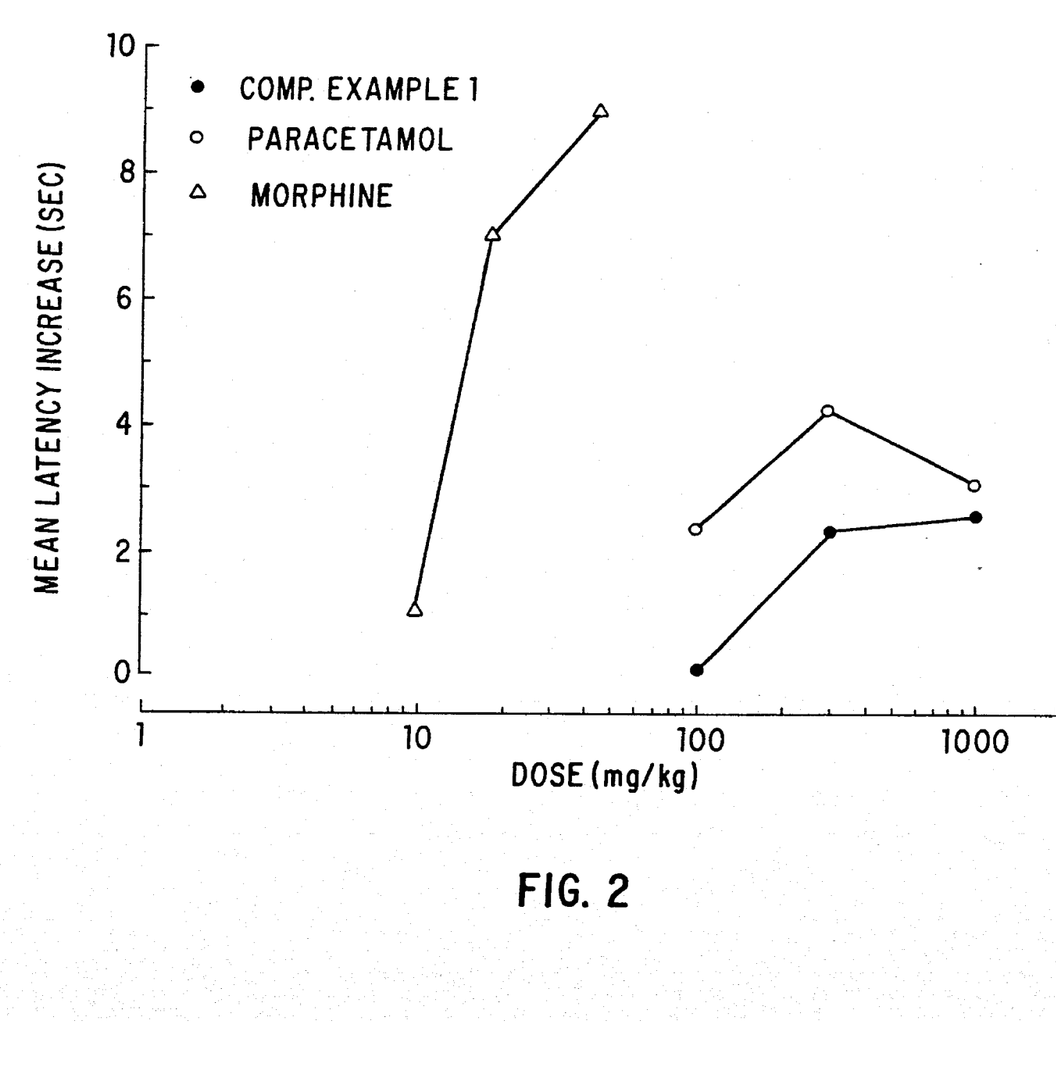
FIG. 2 is the analgesic effect of the hotplate test.
Figure 3:
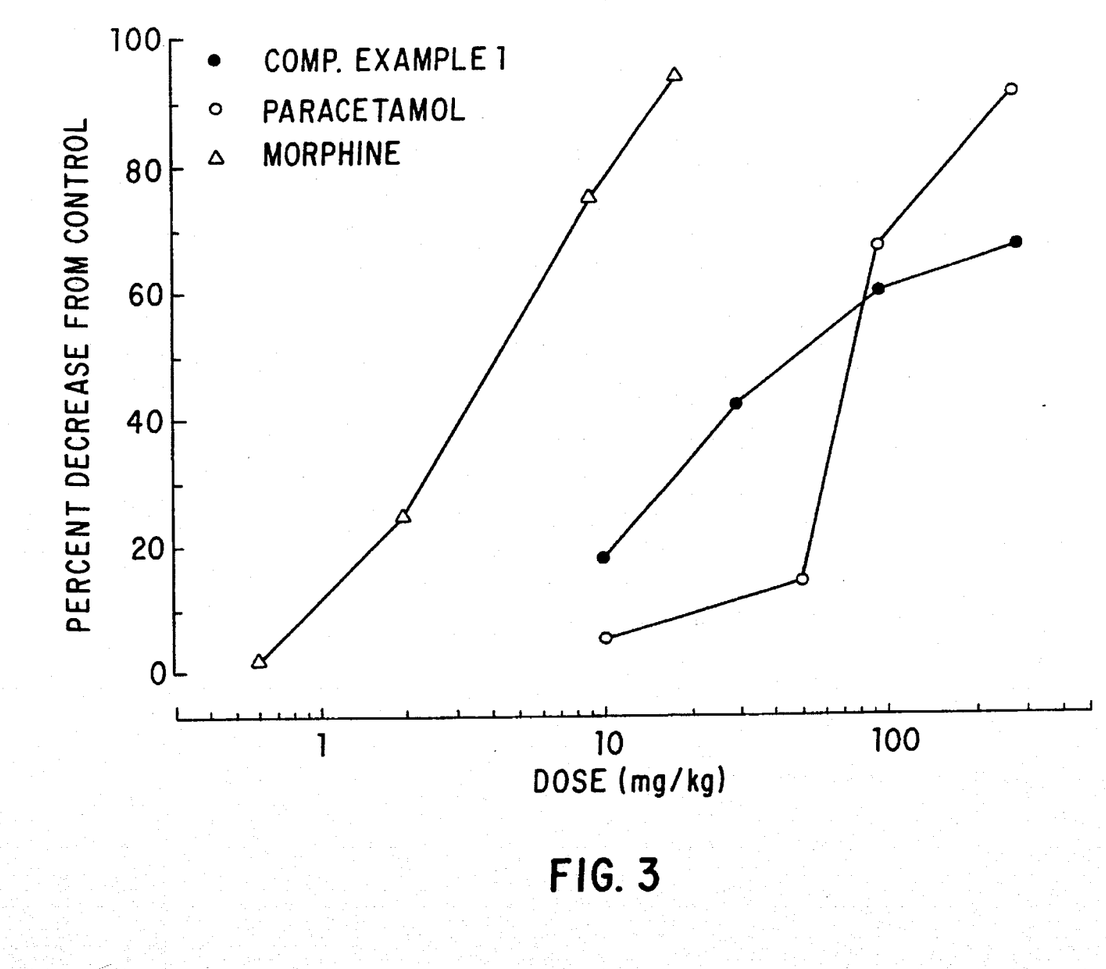
FIG. 3 is the analgesic effect of the acetic acid test.

The results of the three methods are given in FIGS. 1, 2 and 3, respectively.

Antipyretic activity was determined in Sprague-Dawley rats weighing 130–220 g. The animals were injected subcutaneously with a 15% suspension of yeast dissolved in saline solution (1 mL/100 g body weight). Body temperature was measured by means of a rectal thermistor connected to a Cole-Palmer remote thermometer. The temperature at which the experiment was started was the temperature determined 2 hours after the administration of yeasts. Temperature measurements were subsequently made in animals to which paracetamol (standard) or the test compound was administered orally (Suspension K, Bioservel. The results, expressed as the percentage increase in temperature from the baseline value to that obtained 6 hours after the subcutaneous administration of yeast, are given in FIG. 4.

Toxicity studies were based on the measurement of two parameters: mortality and hepatotoxicity.

Mortality was determined by means of the oral administration of 1 g/kg of paracetamol or the test compound (in Suspension K, Bioserve). For this purpose, the number of mice surviving 18 hours after the administration of each compound was counted.

The results are given in Table 1.

For the hepatotoxicity study, mice were kept fasted overnight. The following morning, the compounds were administered orally under ether anesthesia. Owing to its poor solubility, the compound obtained according to Example 1 was dissolved in dimethyl sulfoxide (560 mg/kg, in 35–40 μL of DMSO). Paracetamol was dissolved in 0.5% tragacanth in saline solution. 24 hours after administration of the compounds, blood was withdrawn from the orbital plexus of the mice anesthetized with ether, and placed in heparinized capillary tubes. The samples were centrifuged at 2000 rpm for 10 minutes, and the plasma glutamic-oxaloacetic transaminase (GOT) and glutamicpyruvic transaminase (GPT) levels were determined spectrophotometrically using Sigma kits. The number of animals used in each group is indicated within each column.

Figure 5A:
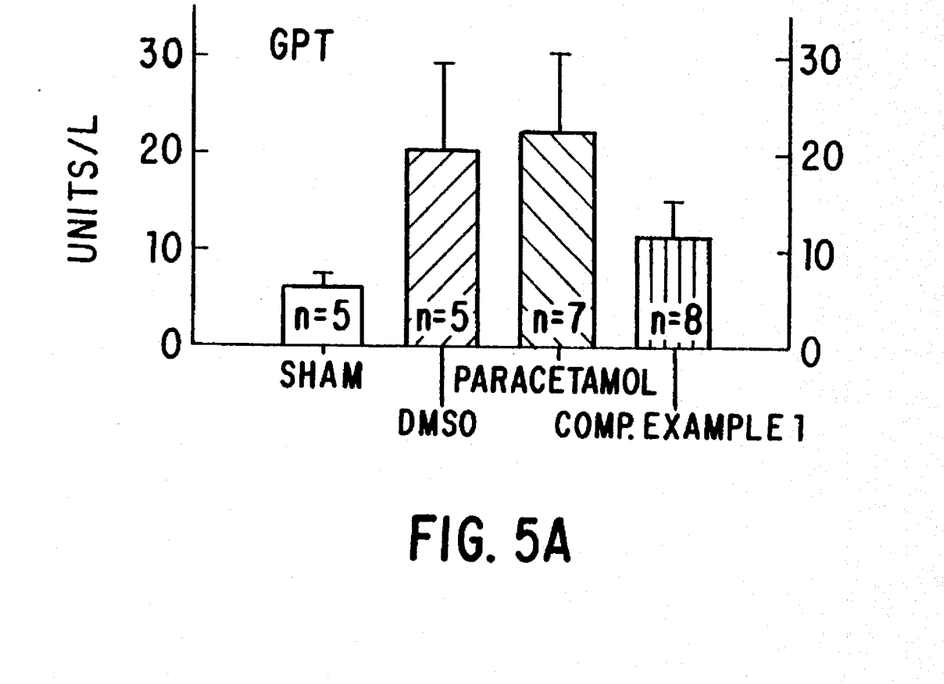
FIG. 5 is the plasma GPT and GOT levels.
Figure 5B:
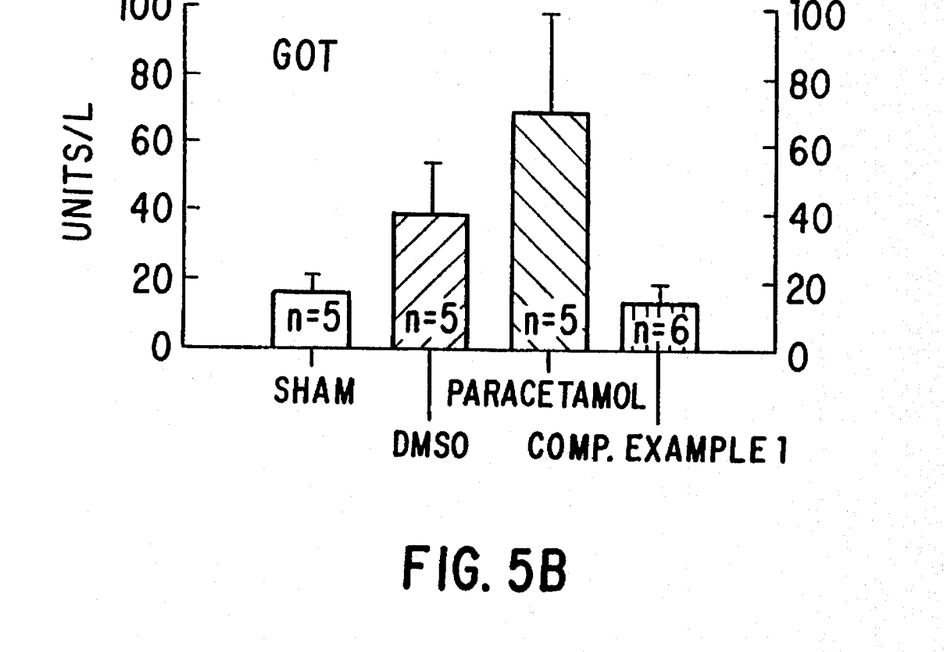

The results are given in FIG. 5.

As may be clearly deduced from the pharmacological tests, the compounds of general formula I of the present invention exhibit considerable analgesic action, do not possess significant antipyretic effects and display, moreover, little hepatotoxic activity.

EXAMPLES

The following non-limiting examples illustrate the present invention.

Example 1

2-[2,3-Dihydro-3-oxo-1,2-benzisothiazol-2-yl 1,1-dioxide]-N-(4-hydroxyphenyl)acetamide A solution consisting of 37.12 g (0.2 mol) of 2-chloro-N-(4-hydroxyphenyl)acetamide and 41.03 g (0.2 mol) of saccharin sodium in 200 mL of anhydrous dimethylformamide is heated to reflux with stirring for 3 hours. At the end of this time, the NaCl formed is filtered off and the filtrate is evaporated under reduced pressure. The resulting oil crystallizes in 200 mL of n-hexane/acetone (1:1) and the product thereby obtained is recrystallized in ethanol, as a result of which 57 g (Yld.: 86%) of a crystalline white solid, m.p. 204°–6° C., are finally obtained.

| Analysis for: $C_{15}H_{12}N_2O_5S$ | % C | % H | % N |
|---|---|---|---|
| Calculated | 54.21 | 3.64 | 8.43 |
| Found | 53.88 | 3.75 | 8.36 |

Example 2

3-[2,3-Dihydro-3-oxo-1,2-benzisothiazol-2-yl 1,1-dioxide]-N-(4-hydroxyphenyl)propionamide To a solution, previously cooled to 0° C., consisting of 2.5 g (0.01 mol) of 3-[2,3-dihydro-3-oxo-1, 2-benzisothiazol-2-yl 1,1-dioxide]propionic acid, 1.1 g (0.01 mol) of 4-aminophenol and 1.35 g (0.01 mol) of 1-hydroxy-1H-benzotriazole in 50 mL of anhydrous methylene chloride, another solution consisting of 2.05 g (0.01 mol) of 1,3-dicyclohexylcarbodiimide in 15 mL of anhydrous methylene chloride is added dropwise and with stirring, When the addition is complete, the reaction mixture is kept stirring at room temperature for 2 hours. At the end of this time, the resulting solid is filtered off and purified by means of recrystallization in ethanol/water (1:1). In this way, 2.3 g (Yld.: 70%) of a crystalline solid, m.p. 237°–9° C., are obtained.

| Analysis for: $C_{16}H_{14}N_2O_5S$ | % C | % H | % N |
|---|---|---|---|
| Calculated | 55.48 | 4.07 | 8.08 |
| Found | 55.84 | 4.18 | 7.68 |

Example 3

5-[2,3-Dihydro-3-oxo-1,2-benzisothiazol-2-yl 1,1-dioxide]-N-(4-hydroxyphenyl)pentanamide To a solution, previously cooled to 0° C., consisting of 2.8 g (0.01 mol) of 5-[2,3-dihydro-3-oxo-1, 2-benzisothiazol-2-yl 1,1-dioxide]pentanoic acid, 1.1 g (0.01 mol) of 4-aminophenol and 1.35 g (0.01 mol) of 1-hydroxy-1H-benzotriazole in 50 mL of anhydrous methylene chloride, another solution consisting of 2.05 g (0.01 mol.) of 1,3-dicyclohexylcarbodiimide in 15 mL of anhydrous methylene chloride is added dropwise and with stirring. When the addition is complete, the reaction mixture is kept stirring at room temperature for 2 hours. At the end of this time, the resulting solid is filtered off and purified by means of recrystallization in ethanol/water (1:1). In this way, 2 g (Yld.: 54%) of a crystalline solid, m.p. 162°–4° C., are obtained.

| Analysis for: $C_{18}H_{18}N_2O_5S$ | % C | % H | % N |
|---|---|---|---|
| Calculated | 57.74 | 4.85 | 7.48 |
| Found | 58.04 | 4.93 | 7.19 |

Example 4

6-[2,3-Dihydro-3-oxo-1,2-benzisothiazol-2-yl 1,1-dioxide]-N-(4-hydroxyphenyl)hexanamide To a suspension, previously cooled to 0° C., consisting of 7.74 g (0.026 mol) of 5-[2,3-dihydro-3-oxo-1, 2-benzisothiazol-2-yl 1,1-dioxide]hexanoic acid, 2.84 g (0.026 mol) of 4-aminophenol and 3.52 g (0.026 mol) of 1-hydroxy-1H-benzotriazole in 260 mL of anhydrous methylene chloride, a solution consisting of 5.36 g (0.026 mol) of 1,3-dicyclohexylcarbodiimide in 70 mL of anhydrous methylene chloride is added dropwise and with stirring. When the addition is complete, the reaction mixture is kept stirring at room temperature for 3 hours. At the end of this time, the insoluble solid is removed by filtration and the solvent is evaporated off from the filtrate under reduced pressure. The residue obtained is purified by means of recrystallization in ethanol/water (1:1). In this way, 6 g (Yld.: 60%) of a crystalline solid, m.p. 131°–3° C., are obtained.

| Analysis for: $C_{19}H_{20}N_2O_5S$ | % C | % H | % N |
|---|---|---|---|
| Calculated | 58.75 | 5.19 | 7.21 |
| Found | 58.46 | 5.11 | 7.01 |

ANTIPYRETIC EFFECT:

The injection of yeast increased rectal temperature by 2.46°±0.08° C. (±SEM; n=5 rats).

Figure 4:
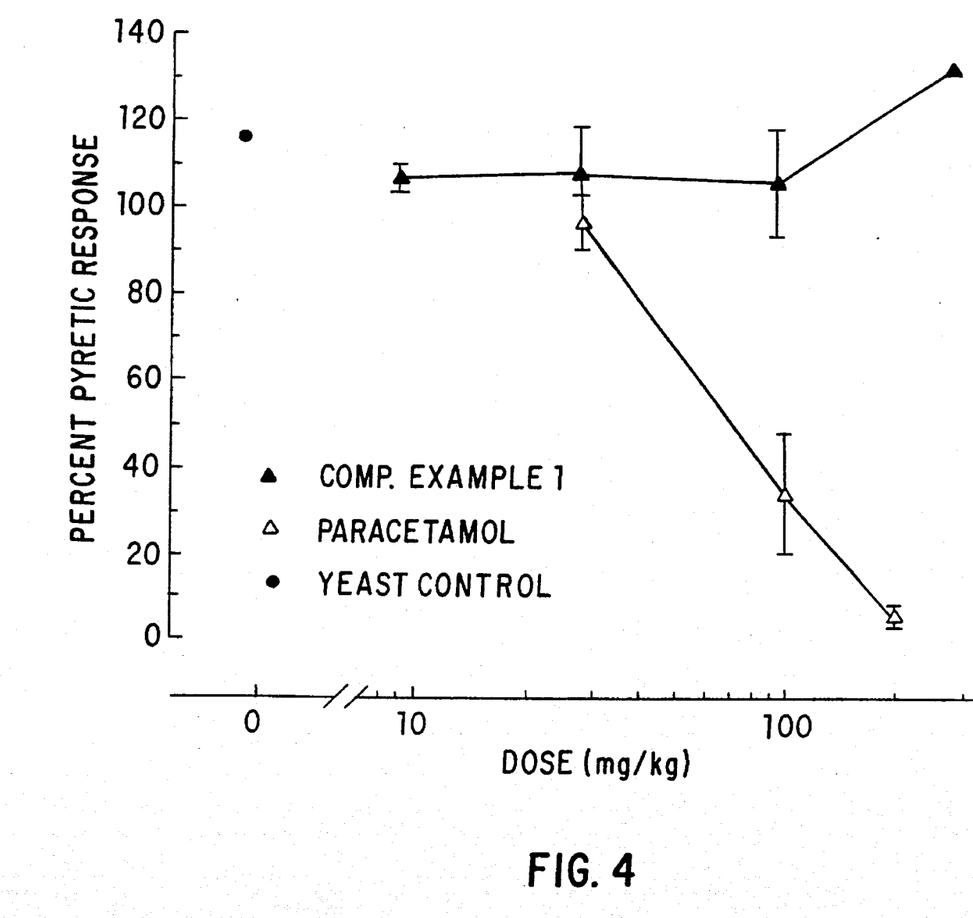
FIG. 4 is the precent pyretic response versus dosage.

Paracetamol reduced the pyretic response in a dose-dependent manner, with an $ED_{50}$=77.7 mg/kg. The product obtained according to Example 1 did not display antipyretic effects at the doses studied (FIG. 4).

TOXICITY:

Table 1 illustrates the results for mortality obtained in mice to which the compound obtained according to Example 1 or paracetamol was administered orally at a dose of 1 g/kg body weight.

18 hours after administration, only one of the 11 mice treated with paracetamol survived. All 10 mice to which the compound obtained according to Example 1 was administered survived.

TABLE 1

| Drug | Survivors/Total |
|---|---|
| Comp. obtained according to Example 1 | 10/10 |
| Paracetamol | 1/11 |

Moreover, the oral administration of paracetamol to mice (550 mg/kg in 0.5% tragacanth) produced a marked increase in the plasma GPT and GOT transaminase levels (FIG. 5). Dimethyl sulfoxide (DMSO) alone produced a substantial rise in both transaminases. However, the administration of the compound obtained according to Example 1, dissolved in DMSO (560 mg/kg in 35–40 µL of DMSO), did not modify the baseline GOT levels, and actually reduced the rise in GPT levels produced by the administration of DMSO (FIG. 5).

In summary, it should be stressed that the compound obtained according to Example 1 possesses an analgesic activity equivalent to that of paracetamol but, in contrast to the latter, possesses much lower toxicity and, of even greater importance, lacks hepatotoxicity. Furthermore, said compound has the great advantage of not possessing antipyretic effects, since antipyresis can mask the presence of latent infections during the post-operative period. For this reason, a clear indication of the compound obtained according to Example 1 would be in the treatment of pain following surgery. To this should be added the general indications for paracetamol as an analgesic, without the serious risk incurred by the production of hepatotoxicity by this drug when used at high doses.

We claim:
1. A process for preparing a compound of formula I comprising:
reacting a compound of formula IV, wherein n is a number from 1 to 5, with 4-aminophenol, to give a compound of formula I.

* * * * *

UNITED STATES PATENT AND TRADEMARK OFFICE
CERTIFICATE OF CORRECTION

PATENT NO. : 5,621,110
DATED : April 15, 1997
INVENTOR(S) : Nicolas G. Bazan

It is certified that error appears in the above-indentified patent and that said Letters Patent is hereby corrected as shown below:

Title page, Col. 1, item [54], in line 2 of the title, "4-HYDROXYPENYLAMINE" should read "4-HYDROXYPHENYLAMINE".

Signed and Sealed this

First Day of July, 1997

Attest:

Attesting Officer

BRUCE LEHMAN

Commissioner of Patents and Trademarks